United States Patent
Jabir et al.

(10) Patent No.: US 12,007,347 B2
(45) Date of Patent: Jun. 11, 2024

(54) SENSOR

(71) Applicant: Oxford Brookes University, Oxford (GB)

(72) Inventors: Abusaleh Jabir, Oxford (GB); Saurabh Khandelwal, Oxford (GB); Xiaohan Yang, Oxford (GB)

(73) Assignee: OXFORD BROOKES UNIVERSITY (GB)

( * ) Notice: Subject to any disclaimer, the term of this patent is extended or adjusted under 35 U.S.C. 154(b) by 0 days.

(21) Appl. No.: 17/754,484

(22) PCT Filed: Oct. 2, 2020

(86) PCT No.: PCT/GB2020/052438
§ 371 (c)(1),
(2) Date: Apr. 4, 2022

(87) PCT Pub. No.: WO2021/064423
PCT Pub. Date: Apr. 8, 2021

(65) Prior Publication Data
US 2024/0053288 A1  Feb. 15, 2024

(30) Foreign Application Priority Data

Oct. 2, 2019  (GB) ..................................... 1914221

(51) Int. Cl.
*G01N 27/06*   (2006.01)
*G01N 27/04*   (2006.01)

(52) U.S. Cl.
CPC ........... *G01N 27/045* (2013.01); *G01N 27/06* (2013.01)

(58) Field of Classification Search
CPC ............................. G01N 27/045; G01N 27/06
(Continued)

(56) References Cited

U.S. PATENT DOCUMENTS

| 2012/0026776 A1* | 2/2012 | Yang | G11C 13/0069 |
| | | | 257/E45.001 |
| 2019/0227017 A1* | 7/2019 | Jabir | G01N 27/041 |

FOREIGN PATENT DOCUMENTS

| CN | 101688905 B | * | 1/2014 | ........... G01R 33/287 |
| CN | 102891679 B | * | 5/2015 | |

(Continued)

OTHER PUBLICATIONS

Wen et al., "A Novel Memristor-Based Gas Cumulative Flow Sensor," in IEEE Transactions on Industrial Electronics, vol. 66, No. 12, pp. 9531-9538, Dec. 2019, doi: 10.1109/TIE.2019.2891436 (Year: 2019).*

(Continued)

*Primary Examiner* — Tung X Nguyen
*Assistant Examiner* — Robert P Alejnikov, Jr.
(74) *Attorney, Agent, or Firm* — William J. Clemens; Shumaker, Loop & Kendrick, LLP

(57) ABSTRACT

A sensor comprises a group of four memristors arranged in an array. Two of the memristors are connected in series as a first pair, and the other two memristors are connected in series as a second pair. The first and second pairs are connected in parallel between two connection points. Each memristor acts as a sensor element because it has an electrical resistance characteristic that is related to exposure to a species to be sensed. In the sensor, the resistance characteristic of the array between the first and second connection points is related to exposure to the species to be sensed. A sensor comprising a larger array can be composed of multiple groups of four memristors.

11 Claims, 4 Drawing Sheets

(58) Field of Classification Search
USPC .......................................................... 324/691
See application file for complete search history.

(56) References Cited

FOREIGN PATENT DOCUMENTS

| DE | 102011085555 A1 * | 5/2013 | ............. G01R 17/10 |
|----|---|---|---|
| WO | 2018065914 A1 | 4/2018 | |

OTHER PUBLICATIONS

Adeyemo et al., "Efficient sensing approaches for high-density memristor sensor array," 17 J. Comp. Elec. 1285 (Apr. 25, 2018), available at https://doi.org/10.1007/s10825-018-1176-y (last accessed Jan. 12, 2024) (Year: 2018).*

Changbao, W. et al., "A novel exposure senor based on reverse series memristor", Senors and Actuators A: Physical, May 18, 2018, pp. 25-32, vol. 278, Elservier B.V., Amsterdam, NL.

Freitas, P. et al., "Spintronic Sensors" Proceedings of the IEEE, Oct. 2016, pp. 1894-1918, vol. 104, No. 10, IEEE, New York, NY, US.

Vidis, M. et al., "Gasistor: A memristor based gas-triggered switch and gas sensor with memory", Applied Physics Letters, Aug. 28, 2019, all pages, vol. 115, No. 9, AIP Publishing LLC, Melville, NY, US.

Yang, C. et al., "On Learning With Nonlinear Memristor-Based Neural Network and Its Replication", IEEE Transactions on Circuits and Systems-I: Regular Papers, Oct. 2019, vol. 66, No. 10, pp. 3906-3916, IEEE, New York, NY, US.

Changbao, W. et al., "A Novel Memristor-Based Gas Cumulative Flow Sensor", IEEE Transactions on Industrial Electronics, Dec. 2019, Voil. 66, No. 12, pp. 9531-9538, IEEE, New York, NY, US.

PCT International Search Report and ISR dated Dec. 18, 2020.

United Kingdom Search Report dated Jan. 17, 2020.

\* cited by examiner

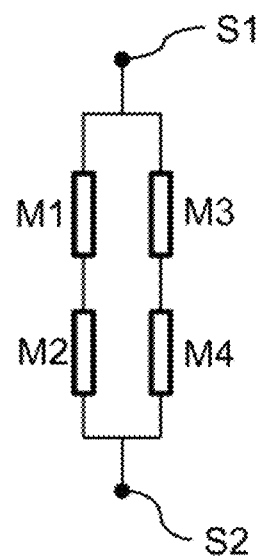
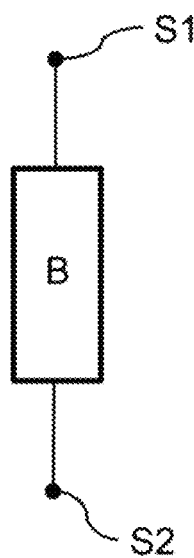
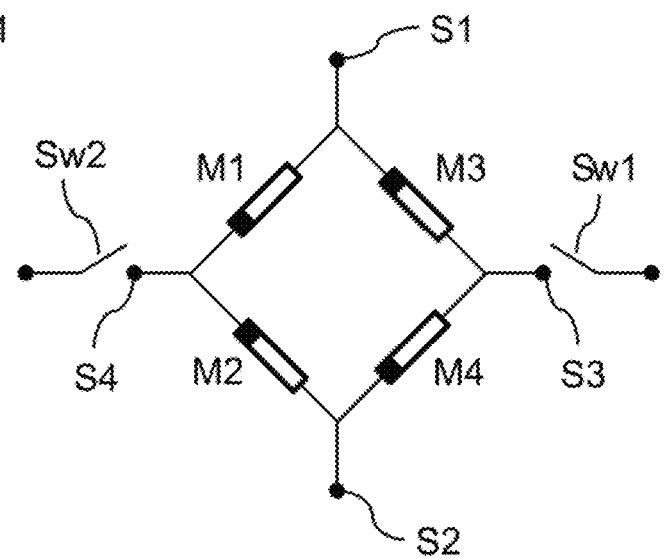
Fig. 1  Fig. 2  Fig. 3
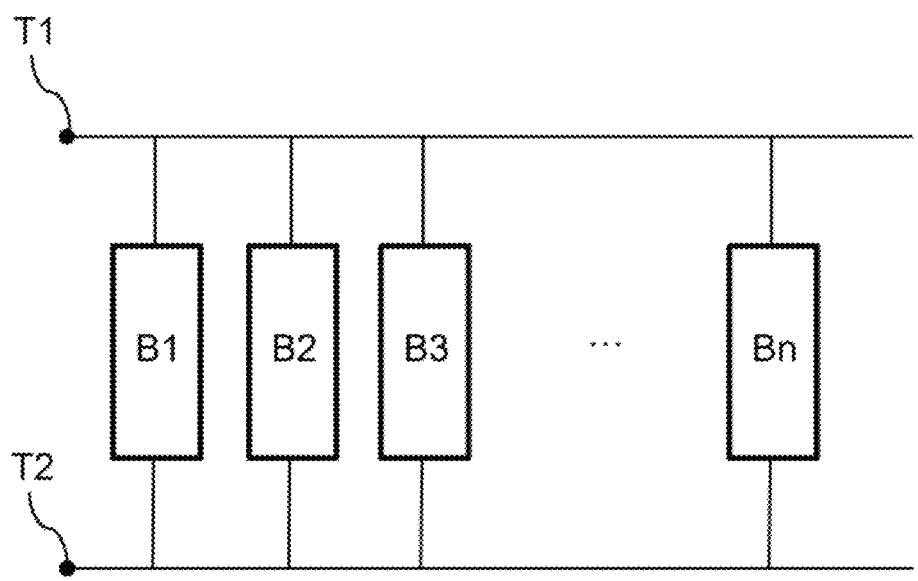
Fig. 4

SENSOR

The present invention relates to a sensor comprising an array of memristive sensor elements, such as for sensing chemical species.

The use of a single memristor (short for 'memory-resistor') as a gas sensor has been proposed. Furthermore, arrays of sensing elements, such as memristors, have been proposed, for example in a crossbar array. In this arrangement, there are a plurality of row wires and a plurality of column wires, and a sensing element is connected between the row wire and column wire at each intersection. If the row wires are connected to each other, and the column wires connected to each other, then all the sensor elements are connected in parallel. This can help average out the readings of many individual sensor elements.

However, there are problem with this conventional arrangement. For example: it is not particularly fault-tolerant to failure of a sensing element: it is difficult to replace a single failed element (typically a whole row or column may have to be substituted or circumvented): a parallel array can have poor power performance; and, in a parallel array, the overall sensitivity as a sensor can shift as the number of sensing elements is changed.

The present invention has been devised in view of the above problems.

Accordingly, one aspect of the present invention provides a sensor comprising:
 a plurality of sensor elements arranged in an array,
 wherein each sensor element is a memristor that has an electrical resistance characteristic related to exposure to a species to be sensed, and
 wherein the array comprises at least one memristor group,
 wherein each said memristor group comprises four memristors, wherein the four memristors are connected as a first pair of two memristors in series, and a second pair of two memristors in series, and with the first pair and second pair connected in parallel between first and second connection points, and
 wherein a resistance characteristic of the array between the first and second connection points is related to exposure to the species to be sensed.

According to an optional aspect of the above invention, the sensor is configured wherein the two memristors of said second pair are connected in series such that the negative terminals of both of them are connected together to a third connection point, and wherein the two memristors of said first pair are connected in series such that the positive terminals of both of them are connected together to a fourth connection point.

Another aspect of the invention provides a method of setting a sensor as defined in the above optional aspect, the method comprising: applying a predetermined positive voltage to the third connection point for a period of time, followed by a negative voltage pulse: and applying a predetermined negative voltage to the fourth connection point for a period of time, followed by a positive voltage pulse.

Further aspects of the invention are defined in the dependent claims.

Embodiments of the invention will now be described, by way of example only, with reference to the accompanying drawings, in which:

FIG. 1 is a circuit diagram of a memristor group of a sensor according to an embodiment of the invention;

FIG. 2 is a circuit symbol equivalent to the memristor group of FIG. 1:

FIG. 3 is a circuit diagram of a memristor group equivalent to FIGS. 1 and 2 showing details according to a further specific embodiment of invention;

FIG. 4 is a schematic diagram of a sensor comprising a parallel array of memristor groups of FIG. 2:

Figure 7:
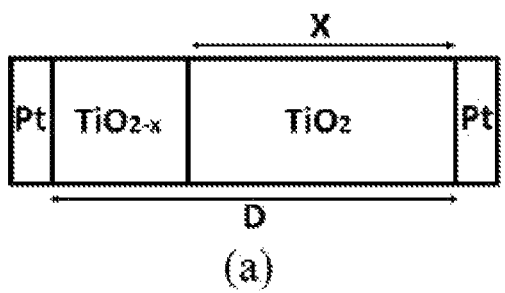
Figure 7:
Figure 8A:
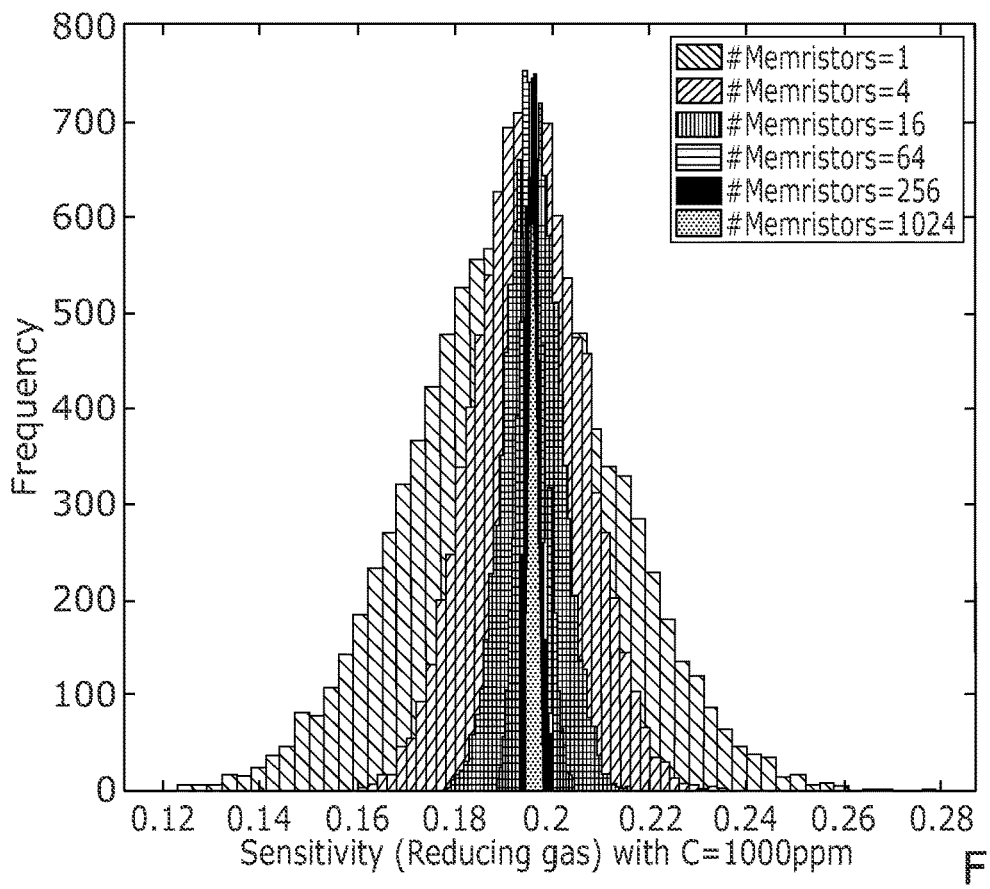
Figure 8B:
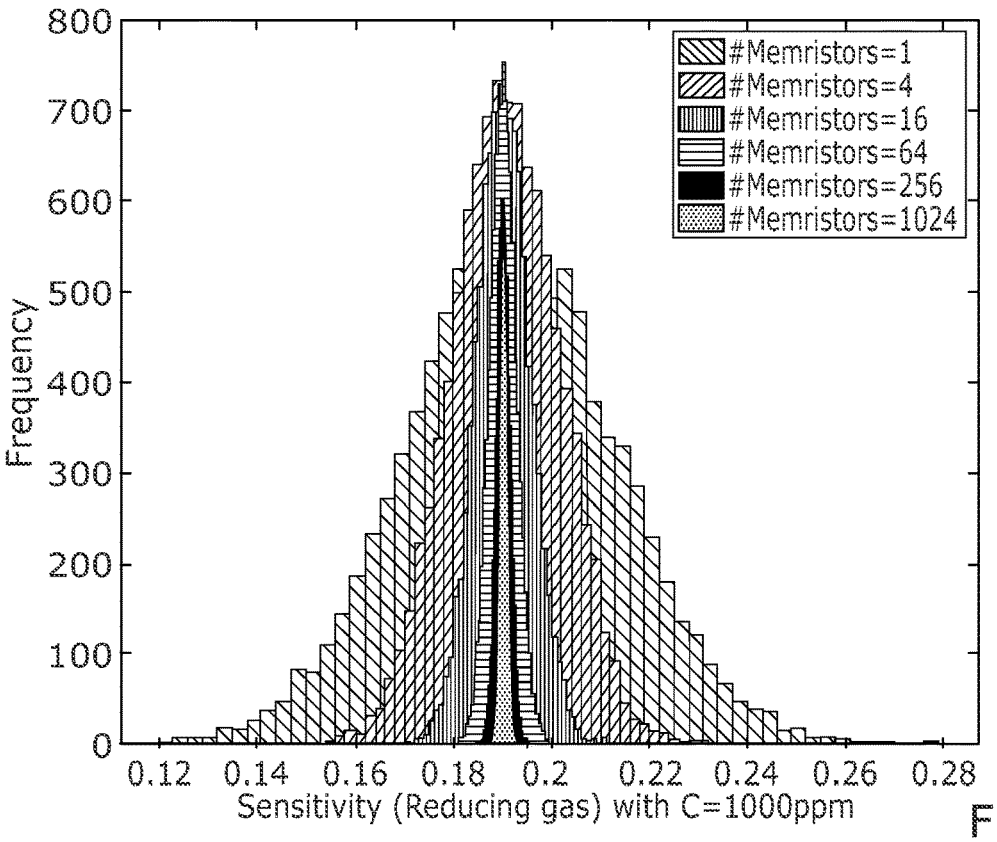
Figure 9:
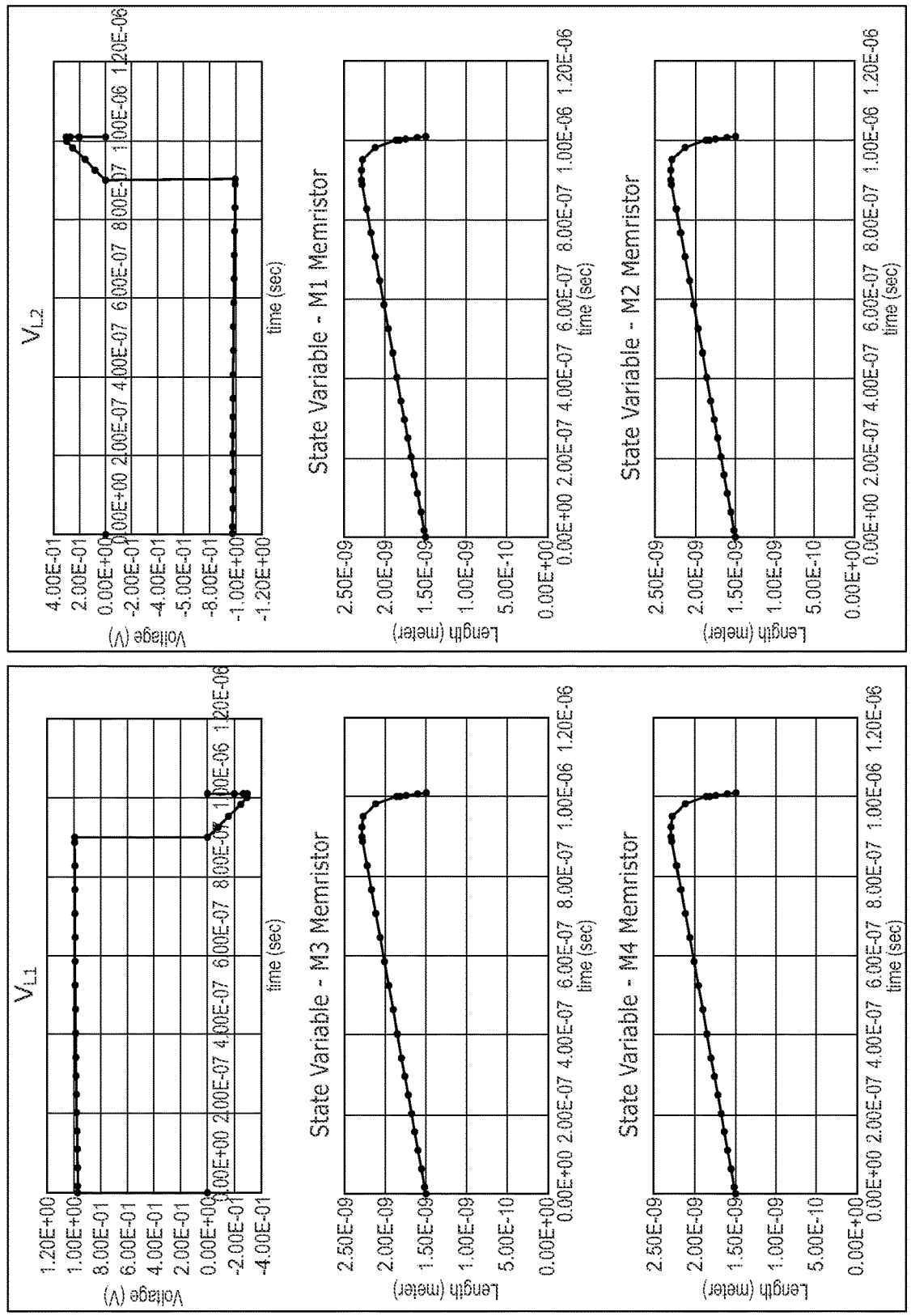

FIGS. 7(a) and 7(b) show the structure of a $TiO_2$-based memristor and the corresponding circuit symbol, respectively:

FIGS. 8(a) and 8(b) are plots of the variations in gas sensitivity of sensors with different numbers of memristor sensing elements having a spread of component parameters, for a conventional parallel array (FIG. 8(a)), and for a recursive architecture embodying the invention (FIG. 8(b)); and FIG. 9 shows graphs of applied voltage against time and the corresponding shift in the state variable (i.e. length x of a memristor depicted in FIG. 7(a)) for the four memristors in a circuit of FIG. 3.

Memristors are known in the art as devices whose electrical resistance is changed by the electrical current that flows through the device. The resistance has a minimum value $R_{ON}$ and a maximum value $R_{OFF}$. The resistance can be switched by application of appropriate voltage or current, and is non-volatile (the resistance value is 'remembered'), so that a memristor can be used as a memory element.

It is also known that memristors can be used as sensing elements because their resistance characteristics can change on exposure to something that is to be sensed. More details of this property are discussed below.

Sensors: Memristor Arrays

FIG. 1 shows a memristor group constituting the simplest unit of an array of memristors for a sensor according to one embodiment of the invention. The memristor group comprises four memristors M1, M2, M3, M4. The memristors M1 and M2 form a first pair connected in series, and the memristors M3, M4 form a second pair connected in series. The first pair and second pair are then connected in parallel between a first connection point S1 and a second connection point S2. FIG. 2 shows a symbol representing the four-memristor group of FIG. 1, and denoted 'B' because it may also be referred to as a 'block' or 'bridge' circuit. In either case, in use, the resistance characteristic is measured between connection points S1 and S2 for the device to function as a sensor.

FIG. 3 shows details of a memristor group according to one specific embodiment of the invention. Each memristor is indicated with a black band at one end to denote a 'positive' terminal: the other end of each memristor being the 'negative' terminal (a memristor is not reversible and so has a 'polarity', though the terms 'positive' and 'negative' are arbitrary labels: again this is discussed further below). In this embodiment, the second pair of memristors M3, M4 are connected such that their negative terminals are connected together to a third connection point, and the first pair of memristors M1, M2 are connected such that their positive terminals are connected together to a fourth connection point S4. As will be understood, this circuit of FIG. 3 is essentially identical to FIG. 1, except that the polarity of the memristors is specified and connection is available to the intermediate points S3, S4. In a preferred embodiment, switches Sw1 and Sw2 are provided such that when the switches are closed, desired voltages can be applied to the connection points S3 and S4, and when the switches are open the connection points can be left floating. This operation will be explained further below. The switches can be implemented in various ways, for example as solid state devices on a chip. The symbol of FIG. 2 is also be used to represent the circuit of FIG. 3, but for simplicity in FIG. 2 and in the rest of the drawings, the additional connection points S3 and S4 not explicitly illustrated.

FIG. 4 shows an array of sensor elements according to a further embodiment of the invention, comprising a plurality of memristor groups B1, B2, B3, . . . Bn connected in parallel. The overall resistance characteristic is measured between terminals T1 and T2 for the device to function as a sensor.

Figure 5:
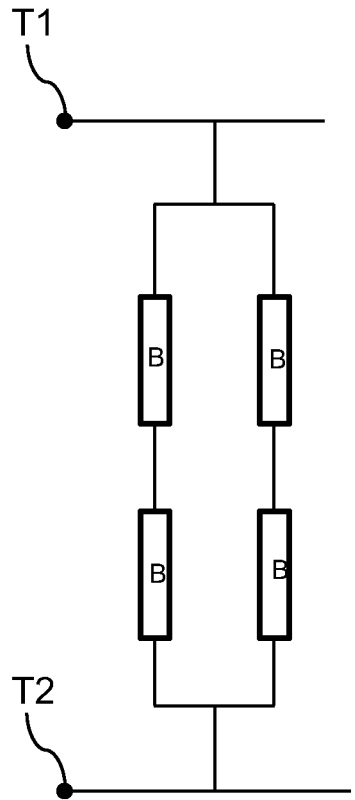
FIG. 5 is a circuit diagram of a sensor comprising a recursive array of memristor groups.

FIG. 5 shows another embodiment of the invention whose structure or circuit architecture is formed in a recursive manner. Starting from, say, the memristor group arrangement of FIG. 1, each of the four memristors is itself replaced with a further memristor group B comprising four memristors. If the groups B of FIG. 5 are redrawn explicitly to show the individual memristors, then the result is FIG. 6, in which it can be seen that there are 16 memristors M. So the circuit of FIG. 6 is identical to FIG. 5, and in either case the overall resistance characteristic is measured between terminals T1 and T2 for the device to function as a sensor.

Figure 6:
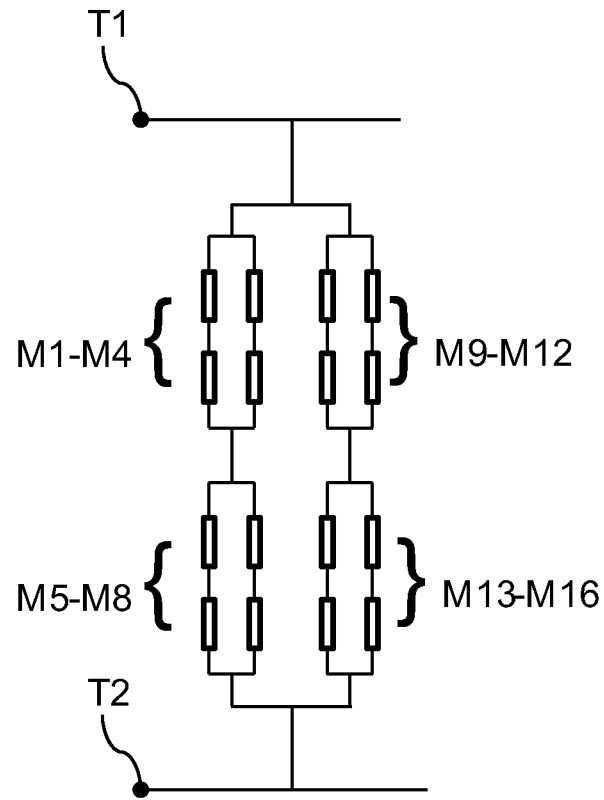
FIG. 6 shows the sensor of FIG. 5 expanded to show each of the individual memristors.

The recursion of the architecture can be iterated a plurality of times, i.e. replacing each of the memristors of FIG. 6 with a group of four memristors arranged as FIG. 1, and so forth repeatedly. The number of memristors quadruples on each iteration. This will yield successive sensor arrays with 16, 64, 256, 1024 . . . etc memristors.

A further embodiment of the invention envisages a mixed array comprising a plurality of recursive arrays (such as FIGS. 5 & 6) arranged in parallel (as in FIG. 4 replacing each group B with a recursive architecture).

MEMRISTOR PROPERTIES

Memristors can be made of various materials, such as: $TiO_2$ (for example with doped and undoped regions and with Pt electrodes): Ag/Ag$_5$In$_5$Sb$_{60}$Te$_{30}$/Ta: Ag-a-LSMO-Pt (Ag nano-filaments in amorphous manganite thin films): other metal oxide semiconductors, such as aluminium oxide, copper oxide, silicon oxide, zinc oxide, tantalum oxide, hafnium oxide: amorphous perovskite oxides (such as a-Sr-TiO$_3$); as well as other ferroelectric and doped polymeric materials, and also graphene oxide. Embodiments of the present invention are not limited to any specific material, provided the memristive property is present. A component that acts as a memristor is described herein as being memristive.

Embodiments of the invention can comprise a highly dense array of nanoscale memristors, for example in the form of thin films, fabricated by lithographic techniques used in microelectronics such as for making memory chips (integrated circuits, ICs). The connections between the memristors can be fabricated on the chip as nanowires. Each memristor acts as a sensor element, and the memristors in the array collectively act as the overall sensor.

FIG. 7(a) shows the structure of one form of memristor, comprising metal oxide. The overall resistance of the memristor is determined by the resistance of two regions: an 'undoped' region $TiO_2$, and a 'doped' region $TiO_{2-x}$, as shown. $TiO_{2-x}$ is a p-type semiconductor and its resistivity decreases in the presence of oxidizing gases, and its resistivity increases in the presence of reducing gases. Metal electrodes, such as platinum, are provided at each end of the device to form 'positive' and 'negative' terminals indicated P and N in FIG. 7(b). FIG. 7(b) shows the symbol of a memristor. In the convention used herein, the dark band indicates the 'positive' terminal, and the other terminal is the 'negative' terminal. If the voltages applied to the positive and negative terminals are $V_p$ and $V_n$ respectively, then the memristor switches to low resistance $R_{ON}$ when $V_p - V_n > V_M$, where $V_M$ is a threshold value which is characteristic of the memristor (memristive device); and it switches to a high resistance $R_{OFF}$ otherwise. The terms 'positive' and 'negative' used herein are purely labels to distinguish the terminals of the memristor, and to define the switching behavior above: in the art the terminals may also be given other labels such as in/out, active/inactive, input/output, +/−.

The total length of the device between the electrode is indicated D (typically 3 nm in one particular device), and the boundary between the two regions of the device is at position x. The value of x is also referred to as the 'state variable' of the memristor. The position x can be changed by passage of current through the device (achieved by the application of appropriate voltages to the electrodes) and is part of the memristive effect. When x=0, the entire device is in a low resistive state (LRS) with minimum resistance value $R_{on}$. When x=D, the entire device is in a high resistive state (HRS) with maximum resistance value $R_{off}$.

Non-Linear Gas Sensor Model

In use as a sensor to sense a target species (such as a gas, liquid or chemical entity in solution), the interaction of a target species with the exposed surface of the metal oxide results in a change in the resistivity in the material without affecting the position of the state variable. The resistance of the device can be modelled, considering firstly the effect of exposure of only that region of the memristor that contributes to the LRS or $R_{on}$, and becomes $R_{onEff}$ upon exposure. The relationship between $R_{on}$ and $R_{onEff}$ is as follows.

$$\frac{R_{On\,Eff}}{R_{On}} = 1 + AC^\beta \quad \text{[Reducing gas]}, \tag{1}$$

$$\frac{R_{On\,Eff}}{R_{On}} = \frac{1}{1 + AC^\beta} \quad \text{[Oxidising gas]}, \tag{2}$$

where A and β are fitting parameters. The model uses Eq. (3) and Eq. (4) to compute initial memristance $R_M^I$ and final memristance $R_M^F$ of the device after exposure to C ppm (parts per million) of gas, $$R_M^I = R_{on} \cdot e^{\lambda_I \cdot (x - x_{on})/(x_{off} - x_{on})} \tag{3}$$

$$R_M^F = R_{onEff} \cdot e^{\lambda_F \cdot (x - x_{on})/(x_{off} - x_{on})}, \tag{4}$$

where $$\lambda_I = \ln\left(\frac{R_{off}}{R_{on}}\right), \quad \lambda_F = \ln\left(\frac{R_{off}}{R_{On\,Eff}}\right), \quad x_{on} \le x \le x_{off}.$$

Here $\lambda_I$ and $\lambda_F$ are fitting parameters, xon is lower bound of undoped region, $x_{off}$ is upper bound of undoped region, and $R_{onEff}$ is as defined in Eq. (1) and Eq.(2) for reducing and oxidizing gas respectively.

In a similar manner the model can also be adopted to accommodate the effects of gas on the High Resistive state or $Ro_{off}$ region in a memristor.

Memristive Amplification

Taking in Eq.(3) and Eq.(4) that $x_{on}=0$ and $x_{off}=D$ (FIG. 7(a)), then $$\frac{x - x_{on}}{x_{off} - x_{on}} = \frac{x}{D}$$

where x varies between 0 and D. i.e. from one end of the device to the other in FIG. 7(a). In Eq.(3) and Eq.(4) one can consider $R_{on}$ as being amplified to a new value $_M{}^I$, and $R_{onEff}$ as being amplified to a new value $R_M{}^F$. The 'gain' of this amplification is determined by the position of x with respect to D and $R_{off}$. The position of x can be set by applying specific voltages across the two terminals of the memristor for a specific period of time (explained in more detail below with reference to FIG. 9). This can be expressed in terms of input and output resistances $R_{in}$ and $R_{out}$ respectively, and gain γ.

$$R_{out} = \gamma \cdot R_{in}$$

where $$\gamma = e^{ln(R_{off}/R_{in}) \cdot x/D}$$

Clearly this gain is non-linear.

For a given $R_{in}$, $R_{out}$ will depend on x/D and $R_{off}$. the value of $R_{out}$ will vary between a minimum of $R_{in}$ to a maximum of $R_{off}$, depending on whether x is closer to 0 or to D respectively.

This understanding of memristive devices is very useful in applications such as sensors where the sensed value may need to be amplified to a measurable quantity. In this case the input can be interpreted as $R_{on}$ or $R_{off}$ which changes to an effective value because of an external event, e.g. exposure to gases/chemicals. In Eq.(3) $R_{on}$ is amplified to $R_M{}^I$, while in Eq.(4) $R_{on}$ changes to $R_{onEff}$ because of C ppm of gas, which is amplified to $R_M{}^F$, and so forth.

For example, in a specific embodiment, oxidizing gases will reduce the effective resistance from $R_{on}$ to $R_{onEff}$ as per Eq.(2): the resulting low resistance can be difficult to measure and can result in significant power consumption. Consider the following scenario: $R_{on}=50Ω$, $R_{off}=10KΩ$, and the memristance is left at LRS (x=0). Then by Eq.(4) $R_M{}^F=1.1652$ for a concentration C=100×103 ppm of gas assuming that A=0.42×10$^{-3}$ and B=1. This small resistance (1.16Ω) will be difficult to measure and will consume significant power (large current). This problem can be solved by 'amplifying' the resistance by moving x toward D, e.g. for x=0.5×D nm, $R_M{}^F=108Ω$, and for x=0.8×D nm, $R_M{}^F=1630Ω$, etc., which are much more measurable quantities, so measurability is improved and power consumption is reduced.

Relative Gas Sensitivity

The relative gas sensitivity, S, is defined as follows:

$$S = \frac{|R_M^F - R_M^I|}{R_M^I}. \quad (5)$$

This measure of sensitivity is used throughout the rest of this description.

Effect of Wire Resistance

As microelectronic technology nodes are shrinking, the effects of nano wire resistance are becoming more prominent. In a sensor, the wire resistance can affect sensitivity performance of the sensor. Embodiments of the invention have been modelled taking into account the nano wire resistance of every branch of current in the array (such as in FIG. 6), varying the wire resistance from 1 μΩ to 1mΩ. FIGS. 8(a) & 8(b) show the results of variation in sensitivity with number of sensor elements (memristors) in the array, with each branch of wire assumed to have a resistance of 1 μΩ. FIG. 8(a) shows results for a conventional parallel architecture (crossbar array), and FIG. 8(b) shows results for recursive architectures (e.g. FIGS. 5 & 6) according to embodiments of the invention. One source of variation is the process/parametric variation in the fabrication of the memristors: in both plots, the values of x and D were varied and were assumed to be random in the Gaussian (normal) distribution space. For each sensor design, 10,000 simulation runs were performed, i.e. 10,000 chip fabrications were simulated with process variations per design, and then the sensor sensitivity was calculated for a gas concentration of 1000 ppm reducing gas.

As expected, in both plots, starting with a sensor with a single memristor, the variation in sensitivity exhibits a broad spread. Each time the number of memristors is increased by 4 the variation spread drops (improves) by approximately a factor of 2(i.e. halves). In the case of the conventional parallel architecture, FIG. 8(a), as the number of memristors increases, the overall sensitivity is shifted to the right due to wire resistance. In contrast, with embodiments of the invention (FIG. 8(b)), the overall sensitivity remains centered around the same value (0.19 in this case) and is relatively immune to nano wire resistance. Shifts in sensitivity can have critical consequences in sensing hazardous gases/chemicals, so should be avoided. Embodiments of the invention minimize the effects of wire resistance, and with the recursive architecture it is comparable that of a single memristor.

The results for FIG. 8(b) are also presented in the following table (with the ideal values of $R_M{}^I=1KΩ$, $R_M{}^F=1.19KΩ$, so sensitivity S=0.191):

| Gas Conc = 1000 ppm, Reducing, $R_{on}$ = 100Ω, $R_{off}$ = 10 KΩ, Wire Resistance = 1 μΩ | | | | | | | |
|---|---|---|---|---|---|---|---|
| No. of Memristors | Mean Sensitivity | Variations Simulated | Times Improvement | Level, i | Variations Calculated (d/2$^i$) | Mean $R_M{}^I$ | Mean $R_M{}^F$ |
| 1 | 0.191902 | d = 0.0209739 | 1 | 0 | — | 1026.18 | 1218.13 |
| 4 | 0.190614 | 0.0108597 | 1.931351695 | 1 | 0.01048695 | 1013.25 | 1205.12 |
| 16 | 0.190184 | 0.00543401 | 3.859746302 | 2 | 0.005243475 | 1010.67 | 1202.56 |
| 64 | 0.19016 | 0.00274224 | 7.648455277 | 3 | 0.002621738 | 1009.18 | 1201.01 |
| 256 | 0.190167 | 0.00137143 | 15.29345282 | 4 | 0.001310869 | 1008.7 | 1200.51 |
| 1024 | 0.190156 | 0.000686856 | 30.5360949 | 5 | 0.000655434 | 1008.71 | 1200.51 |

Memristor Operation

Memristive behavior can be explained as follows, for a voltage $V_p$ applied to the electrode P (FIG. 7(b)): the memristance switches to HRS ($R_{off}$) when the instantaneous voltage $V_p > V_{off}$ and switches to LRS ($R_{on}$) when $V_p < V_{on}$, as defined in Eq.(6) for $V_{in} = V_p (V_n = 0)$ and where w=D−x:

$$\frac{dw(t)}{dt} = \begin{cases} K_{off}\left(\frac{V_{in}}{V_{off}} - 1\right)^{\alpha_{off}} F_{off}(w) & 0 < V_{off} < V_{in} \\ 0 & V_{on} < V_{in} < V_{off} \\ K_{on}\left(\frac{V_{in}}{V_{on}} - 1\right)^{\alpha_{on}} F_{on}(w) & V_{in} < V_{on} < 0, \end{cases} \quad (6)$$

Further background information on this can be obtained from: S Kvatinsky. M Ramadan, E G Friedman and A Kolodny, "VTEAM: A General Model for Voltage-Controlled Memristors", *IEEE Transactions on Circuits and Systems II: Express Briefs*. vol. 62, no. 8, pp. 786-790, August 2015.

Sensor Operation

Considering a memristor group such as FIG. 3, the four memristors M1-M4 act together as a single sensor. To set the barrier position x (state variable) in each memristor to a desired value (for example so that they are all the same, and so that a value is selected for ease of measurement (see section on 'memristive amplification'), the state variables of the four memristors can first be shifted to D (one end of the memristor) and then back to a desired value. such as 0.5×D, by applying accurate voltages for a precise amount of time via switches Sw1, Sw2 to the third and fourth connection points S3, S4, while the voltages at the first and second connection points S1, S2 are set to zero (e.g. either using switches for those connection points, not shown, or via the rest of the array). FIG. 9 illustrates this process. The top-left plot shows the voltage applied to connection point S3, comprising a positive voltage for 0.9 μs, followed by a short negative pulse. The lower two left-hand plots show the result of this shifting the state variable of memristors M3 & M4 towards D (3 nm) and then back to D/2. Similarly, the top-right plot shows the voltage applied to connection point S4, comprising a negative voltage, followed by a short positive pulse. The lower two right-hand plots show the result of this shifting the state variable of memristors M1 & M2 towards D (3 nm) and then back to D/2.

To read a sensed value, a non-zero voltage needs to be applied across the memristor group to allow a current to flow through them simultaneously. The memristors need to be placed in a hold state during the read operation to prevent their state variables and resistance from changing. This can be achieved by having the third and fourth connection points S3, S4 floating, and applying a voltage difference $V_{read}$ between the first and second connection points S1 and S2 that satisfies:

$$\max(-V_{on}, V_{off}) < V_{read} < \min(V_{on}, -V_{off})$$

This can be done simultaneously across the whole of an array by selection of an appropriate $V_{read}$ knowing the number of memristor groups in series (i.e. one in FIGS. 1 to 4, two in FIGS. 5 and 6, and more in successive recursions), multiplying $V_{read}$ by that number, and applying that voltage across the terminals T1, T2.

Performance

For an array of N memristors, each having a resistance R. for a conventional parallel architecture, the total resistance falls as 1/N. For a fixed applied voltage, the total current will be proportional to N. Thus the electrical power (ohmic heating) dissipated will be proportional to N. The resistance of a four-memristor group (FIG. 1) is R, the same as that of a single memristor, because of the combination of series and parallel memristors. Therefore the total resistance of a parallel array (FIG. 4) is proportional to N/4, and so the power consumption will be one quarter that of a conventional parallel array for the same number of memristors. For a recursive array (FIGS. 5 & 6 and recursions thereof), the total resistance always remains at R, regardless of how much it is scaled So the power consumption will be 1/N that of a conventional parallel array for the same number N of memristors. For a 'mixed' architecture, i.e. an array of recursive structures connected in parallel, then the power consumption is intermediate between that of the parallel and recursive architectures.

Sensors according to embodiments of the invention can be more fault-tolerant than conventional parallel sensor arrays. For example, in an array embodying the invention, if a memristor fails, whether open-circuit or short-circuit, then sensor array can still continue to function, and in a very large array, such as 1024 memristors, any change in performance would be marginal. In contrast, in a conventional parallel crossbar array (CBA), if a memristor fails as a short-circuit then it shorts the whole sensor, so that the sensor is useless until the individual failed component can be identified and isolated (even if that is possible).

Sensor chips can be provided with spare components, e.g. around the periphery, which can be routed by switchable connections to replace failed components on the chip. However, sensors according to embodiments of the invention can offer better repairability with lower overhead than conventional parallel CBA sensors. For example in a conventional CBA, if one sensor element (memristor) is faulty, then typically either the entire row or column containing that element must be replaced with a spare row or column. In embodiments of the invention, each memristor is in a group of four memristors. If an element is faulty, only that group of four needs to be replaced with a spare group. In contrast, in a 16×16 CBA if a single memristor is faulty, then the entire row may need to be replaced with a 16-memristor spare row. So with a similar hardware overhead of 16 spare memristors, one fault could be repaired with a CBA, but potentially four faults (4 groups of 4 memristors) could be replaced with embodiments of the invention; hence the repairability is much better.

Sensor Device Variants

Each memristor, or a whole array of memristors on a chip, can be provided with a heater (not shown) to raise its temperature to a suitable operating temperature as necessary for the chemical species to be sensed. The heater can also stabilize the temperature to a constant value for consistent measurements.

The gas concentration can be sensed or measured in a variety of ways, as the circumstances dictate, for example by: the absolute resistance of the memristor (in the high or low resistance states, or in an intermediate state): the ratio of high to low resistance: the peak current: differential resistance, and so on; these are all encompassed by the term 'resistance characteristic' of the memristor or memristor array. The resistance characteristic measurements can be performed using DC and/or AC techniques, and with or without bias voltages. Resistance values can be calibrated against known gas concentrations, and provided as a look-up table or as an equation for the sensor to convert electrical measurements to gas concentrations.

The same considerations apply to measuring the resistance characteristic of an array of memristors as for a single memristor.

In general, the interaction of a target chemical species with the surface of each memristor results in a change in the resistivity, and causes a change in output of the associated read circuitry (not shown). Choice of materials for the memristors, such as the oxides mentioned above, and also polymers or porphyrins, means it is possible to select the target species and sensitivity pattern of the sensor. The memristors can also be made selective to sense only one species or a specific group of species, but not others. For example, a sensor embodying the invention could be used to detect volatile compounds and gases, such as nitrogen oxides, carbon monoxide, alcohols, amines, terpenes, hydrocarbons, or ketones, and/or a variety of different gases (oxidizing or reducing). Although the embodiment above referred to sensing species in the gas phase, that is not essential to the invention: embodiments of the invention can also be used to sense liquids or species in liquids (for example ions of Hg, Ca, Pb, Cr), and as biosensors (for example for sensing pesticides, specific proteins, amino acids, or DNA). The structure and measurement technique of the sensor described herein could, in principle, be used in other embodiments to sense physical properties instead of chemical species: for example, as a thermistor for sensing temperature, or as a photoconductor for sensing light, and so on.

All of the above embodiments can include control circuitry (not shown) to apply the required voltages, make the necessary connections, measure the output, and provide a sensing function, such as converting the electrical measurement to a gas concentration value or values. The control circuitry can be dedicated logic and hardware, and/or can include general purpose circuitry, such as a microprocessor running suitable software.

When not in use as a sensor, each group of four memristors (FIG. 3) can also be utilized to act as a logic gate as taught in WO 2017/144862, thereby making the device multifunctional.

Embodiments of the invention can take advantage of highly dense arrays of memristive sensor elements, for example on a microelectronic chip. An array can comprise tens or hundreds of elements, but can also be much larger such as 1024 elements or even more. This makes the sensor compact, robust and low-power. The sensor is particularly suitable for use in portable devices, such as integrating into smart phones, tablet computers, or hand-held sensors.

The invention claimed is:

1. A sensor comprising:
   a plurality of sensor elements arranged in an array;
   wherein each of the sensor elements is a memristor that has an electrical resistance characteristic related to exposure of the memristor to a species to be sensed;
   wherein the array comprises at least one memristor group;
   wherein each said memristor group comprises four of the memristors, wherein the four memristors are connected as a first pair of two memristors in series, and a second pair of two memristors in series, and with the first pair and the second pair connected in parallel between first and second connection points; and
   wherein a resistance characteristic of the array between the first and second connection points is related to exposure of the memristors in the array to the species to be sensed.

2. The sensor according to claim 1 wherein the two memristors of said second pair are connected in series such that the negative terminals of both of them are connected together to a third connection point, and wherein the two memristors of said first pair are connected in series such that the positive terminals of both of them are connected together to a fourth connection point.

3. The sensor according to claim 2 further comprising a first switch to enable a voltage to be applied to the third connection point and a second switch to enable a voltage to be applied to the fourth connection point, said switches also enabling the third and fourth connection points to be floating.

4. A method of setting a sensor, the method comprising the steps of:
   providing the sensor according to claim 2;
   applying a predetermined positive voltage to the third connection point for a period of time, followed by applying a negative voltage pulse to the third connection point; and
   applying a predetermined negative voltage to the fourth connection point for a period of time, followed by applying a positive voltage pulse to the fourth connection point.

5. The sensor according to claim 1 comprising a plurality of the at least one memristor group.

6. The sensor according to claim 5 wherein the memristor groups are connected in parallel.

7. The sensor according to claim 5 comprising a recursive architecture, wherein each memristor in a group of four memristors has been replaced with a further memristor group comprising four memristors.

8. The sensor according to claim 7 wherein the recursion of the architecture is iterated a plurality of times.

9. The sensor according to claim 1 wherein the plurality of sensor elements arranged in the array is formed as a microelectronic structure.

10. The sensor according to claim 1 being fabricated on a chip.

11. The sensor according to claim 1 wherein the sensor is at least one of a gas sensor, a liquid sensor, and a sensor for sensing the species present in a liquid.

* * * * *